United States Patent
Maeso et al.

(10) Patent No.: US 10,124,437 B2
(45) Date of Patent: Nov. 13, 2018

(54) LASER WELDING OF NICKEL TITANIUM ALLOYS

(71) Applicant: COVIDIEN LP, Mansfield, MA (US)

(72) Inventors: Jose Maeso, San Diego, CA (US); Alan Eskuri, Hanover, MN (US)

(73) Assignee: Covidien LP, Mansfield, MA (US)

( * ) Notice: Subject to any disclaimer, the term of this patent is extended or adjusted under 35 U.S.C. 154(b) by 1409 days.

(21) Appl. No.: 13/970,004

(22) Filed: Aug. 19, 2013

(65) Prior Publication Data

US 2015/0048060 A1    Feb. 19, 2015

(51) Int. Cl.
| | |
|---|---|
| *B23K 26/00* | (2014.01) |
| *B23K 26/32* | (2014.01) |
| *B23K 11/20* | (2006.01) |
| *B23K 11/02* | (2006.01) |
| *A61M 25/09* | (2006.01) |
| *B21F 15/08* | (2006.01) |
| *B23K 20/00* | (2006.01) |
| *B23K 26/323* | (2014.01) |
| *B23K 26/0622* | (2014.01) |
| *A61L 31/02* | (2006.01) |

(Continued)

(52) U.S. Cl.
CPC ............ *B23K 11/20* (2013.01); *A61L 31/022* (2013.01); *A61M 25/09* (2013.01); *B21F 15/08* (2013.01); *B23K 11/02* (2013.01); *B23K 20/004* (2013.01); *B23K 26/0622* (2015.10); *B23K 26/323* (2015.10); *A61M 2025/09108* (2013.01); *B23K 2201/32* (2013.01); *B23K 2203/24* (2013.01)

(58) Field of Classification Search
CPC .............. B23K 26/323; B23K 2203/24; B23K 2201/32; B23K 26/0622; B23K 11/11; B23K 11/3009; B23K 10/02; B23K 9/0026; B23K 15/0046; B23K 15/008
USPC ............... 219/121.64, 118, 119, 121.85, 101
See application file for complete search history.

(56) References Cited

U.S. PATENT DOCUMENTS

| | | | | |
|---|---|---|---|---|
| 4,224,499 A | * | 9/1980 | Jones | B23K 28/02 |
| | | | | 219/118 |
| 4,737,612 A | * | 4/1988 | Bruck | B23K 26/242 |
| | | | | 219/121.64 |

(Continued)

FOREIGN PATENT DOCUMENTS

| | | |
|---|---|---|
| JP | H0819883 A | 1/1996 |
| WO | 2012125515 A1 | 9/2012 |

OTHER PUBLICATIONS

International Preliminary Report on Patentability from International Application No. PCT/US2014/050271, dated Mar. 3, 2016, 9 pp.

(Continued)

*Primary Examiner* — Dana Ross
*Assistant Examiner* — Lawrence Samuels
(74) *Attorney, Agent, or Firm* — Shumaker & Sieffert, P.A.

(57) ABSTRACT

A system of forming a bimetal medical device from dissimilar metal components includes a first metal component, a second metal component, a retaining device, a compression mechanism, and an energy source. A method of forming the bimetal medical device with the system includes applying a first pulse of laser energy to a joint formed between the first and second metal components retained by the retaining device and compressing the first and second metal components together with the compression mechanism to form a welded region.

11 Claims, 4 Drawing Sheets

(51) Int. Cl.
   *B23K 101/32* (2006.01)
   *B23K 103/24* (2006.01)

(56) References Cited

U.S. PATENT DOCUMENTS

| | | | |
|---|---|---|---|
| 5,222,654 A * | 6/1993 | Oki | B21B 15/0085 228/205 |
| 5,243,996 A | 9/1993 | Hall | |
| 5,365,943 A | 11/1994 | Jansen | |
| 5,368,661 A | 11/1994 | Nakamura et al. | |
| 5,402,799 A | 4/1995 | Colon et al. | |
| 5,411,476 A | 5/1995 | Abrams et al. | |
| 5,433,200 A | 7/1995 | Fleischhacker, Jr. | |
| 5,636,641 A | 6/1997 | Fariabi | |
| 5,664,580 A | 9/1997 | Erickson et al. | |
| 5,666,969 A | 9/1997 | Urick et al. | |
| 5,682,894 A | 11/1997 | Orr et al. | |
| 5,695,111 A | 12/1997 | Nanis et al. | |
| 5,720,300 A | 2/1998 | Fagan et al. | |
| 5,769,796 A | 6/1998 | Palermo et al. | |
| 5,797,857 A | 8/1998 | Obitsu | |
| 5,828,032 A * | 10/1998 | Krzys | B23K 15/006 219/121.64 |
| 5,865,768 A | 2/1999 | Orr | |
| 6,039,699 A | 3/2000 | Viera | |
| 6,068,623 A | 5/2000 | Zadno-Azizi et al. | |
| 6,352,515 B1 | 3/2002 | Anderson et al. | |
| 6,387,060 B1 | 5/2002 | Jalisi | |
| 6,390,993 B1 | 5/2002 | Cornish et al. | |
| 6,482,166 B1 | 11/2002 | Fariabi | |
| 6,488,637 B1 | 12/2002 | Eder et al. | |
| 6,508,803 B1 | 1/2003 | Horikawa et al. | |
| 6,545,244 B1 * | 4/2003 | Gould | B23K 11/02 219/118 |
| 6,602,207 B1 | 8/2003 | Mam et al. | |
| 6,602,228 B2 | 8/2003 | Nanis et al. | |
| 6,702,762 B2 | 3/2004 | Jafari et al. | |
| 6,845,259 B2 | 1/2005 | Pacetti et al. | |
| 6,875,949 B2 * | 4/2005 | Hall | B23K 35/3053 219/121.63 |
| 6,908,443 B2 | 6/2005 | Burmeister et al. | |
| 6,918,882 B2 * | 7/2005 | Skujins | A61L 31/022 600/585 |
| 7,316,656 B2 | 1/2008 | Shireman et al. | |
| 7,540,845 B2 | 6/2009 | Parins | |
| 7,547,288 B2 | 6/2009 | Murayama et al. | |
| 7,607,561 B2 | 10/2009 | Murayama et al. | |
| 7,632,237 B2 | 12/2009 | Murayama et al. | |
| 7,637,875 B2 | 12/2009 | Itou | |
| 7,641,622 B2 | 1/2010 | Satou et al. | |
| 7,715,903 B2 | 5/2010 | Hartley et al. | |
| 7,717,864 B1 | 5/2010 | Grandfield et al. | |
| 7,722,551 B2 | 5/2010 | Murayama et al. | |
| 7,722,552 B2 | 5/2010 | Aimi et al. | |
| 7,762,962 B2 | 7/2010 | Mishima | |
| 7,770,779 B2 | 8/2010 | Murayama et al. | |
| 7,785,274 B2 | 8/2010 | Mishima et al. | |
| 7,878,984 B2 | 2/2011 | Jacobsen et al. | |
| 7,892,187 B2 | 2/2011 | Murayama et al. | |
| 7,922,673 B2 | 4/2011 | Murayama et al. | |
| 7,955,272 B2 | 6/2011 | Rooney et al. | |
| 7,998,090 B2 | 8/2011 | Simpson et al. | |
| 8,007,447 B2 | 8/2011 | Murayama et al. | |
| 8,124,905 B2 | 2/2012 | Murayama et al. | |
| 8,197,424 B2 | 6/2012 | Nabeshima | |
| 8,348,859 B2 | 1/2013 | Murayama et al. | |
| 8,348,860 B2 | 1/2013 | Murayama et al. | |
| 9,662,745 B2 * | 5/2017 | Yao | B23K 1/0008 |
| 2003/0030373 A1 | 2/2003 | Kawamura et al. | |
| 2003/0216668 A1 | 11/2003 | Howland et al. | |
| 2004/0106878 A1 | 6/2004 | Skujins et al. | |
| 2004/0167438 A1 | 8/2004 | Sharrow | |
| 2004/0167441 A1 * | 8/2004 | Reynolds | A61L 31/022 600/585 |
| 2004/0182835 A1 * | 9/2004 | Hall | B23K 35/3053 219/121.64 |
| 2006/0047223 A1 * | 3/2006 | Grandfield | A61M 25/0905 600/585 |
| 2007/0232957 A1 | 10/2007 | Murayama et al. | |
| 2007/0265553 A1 | 11/2007 | Murayama et al. | |
| 2008/0161728 A1 | 7/2008 | Mishima | |
| 2008/0171217 A1 | 7/2008 | Mishima | |
| 2008/0183182 A1 | 7/2008 | Satou et al. | |
| 2008/0234606 A1 | 9/2008 | Itou | |
| 2008/0269641 A1 | 10/2008 | O'Shaughnessy et al. | |
| 2009/0005706 A1 | 1/2009 | Miyata et al. | |
| 2009/0017328 A1 * | 1/2009 | Katoh | B23K 9/173 428/653 |
| 2009/0182246 A1 | 7/2009 | Kinoshita et al. | |
| 2009/0227902 A1 * | 9/2009 | Simpson | A61M 25/09 600/585 |
| 2010/0286566 A1 | 11/2010 | Griffin et al. | |
| 2011/0230862 A1 | 9/2011 | Segner et al. | |
| 2011/0297658 A1 * | 12/2011 | Peters | B23K 9/02 219/162 |
| 2012/0215300 A1 * | 8/2012 | Richardson | A61F 2/064 623/1.36 |
| 2013/0226033 A1 | 8/2013 | Eskuri | |
| 2013/0341306 A1 * | 12/2013 | Kinefuchi | B23K 9/025 219/74 |
| 2014/0008335 A1 * | 1/2014 | Yao | B23K 1/0008 219/121.64 |

OTHER PUBLICATIONS

Communication Pursuant to Rules 161(1) and 162 EPC dated Apr. 19, 2016, from counterpart European Application No. 14752762.6, 2 pp.

International Search Report and Written Opinion from counterpart International Patent Application No. PCT/2014/050271, dated Feb. 11, 2015, 13 pp.

Examination Report from counterpart European Application No. 14752762.6, dated Jul. 9, 2018, 6 pp.

* cited by examiner

LASER WELDING OF NICKEL TITANIUM ALLOYS

BACKGROUND

Technical Field

The present disclosure relates generally to systems and methods for welding metal components to form medical devices. More particularly, the present disclosure relates to systems and associated methods for laser welding a nickel titanium alloy with a dissimilar metal or metal alloy to form a bimetal medical device.

Description of Related Art

Guidewires are commonly used in medical procedures to assist in the advance and proper positioning of a catheter or other medical device in lumens, vessels, or other cavities of the body. Neurovascular procedures utilizing guidewires include the imaging and treatment of aneurysms, arteriovenous malformations (AVM), and ischemic stroke. The effectiveness of an intravascular guidewire in advancing through tortuous neurovasculature without undesired deformation or kinking is dependent upon a number of factors and design considerations. These factors include, inter alia, the material(s) of fabrication of the guidewire, guidewire dimensions and intended use. Generally, a balance must be achieved to provide the required torsional, lateral, tensile and/or column strengths to enable easy and precise manipulation and steerability in the tortuous vasculature. Guidewires for such endovascular procedures face additional challenges due to the relatively small diameter required to navigate through the narrow and remote locations of the neurovasculature.

A guidewire, for example, may be formed from two materials to provide variable stiffness to the device by having a relatively stiff proximal portion to facilitate pushing of the guidewire through the vasculature and a relatively flexible distal portion to facilitate steering of the guidewire through the vasculature. Various techniques for forming a guidewire with variable stiffness include joining a nickel titanium alloy and a dissimilar metal. Known techniques utilize an intermediate material between the two metal components to achieve a strong joint therebetween, an external sleeve or outer layer to reinforce the joint between the two metal components, or mechanical fasteners to join the two metal components together.

SUMMARY

The systems and methods disclosed herein allow direct welding of a nickel titanium alloy with a dissimilar metal while providing a strong bond between the two metal components without the use of intermediary, reinforcing, or extraneous materials, or the need to specially treat or prepare the metal components prior to welding.

A system in accordance with an embodiment of the present disclosure includes a first metal component, a second metal component, a retaining device, a compression mechanism, and an energy source. The first metal component defines a first longitudinal axis and has a first end portion and the second metal component defines a second longitudinal axis and has a second end portion. The retaining device is configured to retain the first and second end portions of the first and second metal component in an abutting relationship to form a butt joint within a welding window of the retaining device. The compression mechanism is configured to apply an axially inward force to move the first and second metal components axially together after application of energy thereto. The energy source is configured to apply laser energy to the first and second end portions of the first and second metal components within the welding window of the retaining device. The energy applied is determined by the equation:

$$\text{Joules} = 5.9DX$$

wherein D=diameter (mm) of the first metal component and X=0.5-1.5.

The first metal component is formed from a nickel-titanium alloy and the second metal component is formed from a dissimilar metal alloy. In some embodiments, the second metal component is formed from a cobalt chromium alloy, and in some other embodiments, the second metal component is formed from a stainless steel alloy.

The compression mechanism is adapted to move the first and second metal components together a distance that is about 0.5 to about 2 times the diameter of the first metal component. In embodiments, the retaining device includes a first fixation member for retaining the first metal component and a second fixation member for retaining the second metal component.

The system may include a rotation mechanism that is configured to rotate the first and second metal components between pulses of the laser energy emitted from the energy source.

An embodiment of a method of forming a bimetal medical device of the present disclosure includes applying a first pulse of laser energy to a butt joint formed between abutting first and second end portions of first and second metal components aligned along a common axis, and compressing the first and second metal components axially together to form a welded region between the first and second metal components. The energy applied during the first pulse is determined by the equation:

$$\text{Joules} = 5.9DX$$

wherein D=diameter (mm) of the first metal component and X=0.5-1.5.

The first and second metal components are moved a distance that is about 0.5 to about 2 times a diameter of the first metal component in the compressing step.

In embodiments, a second pulse of laser energy may be applied to the welded region of the first and second metal components. In certain embodiments, the first and second metal component may be rotated before applying the second pulse of laser energy.

In accordance with another aspect of the present disclosure, a system of forming a bimetal medical device includes a first metal component defining a first longitudinal axis, a second metal component defining a second longitudinal axis, a retaining device configured to retain at least a portion of the first and second metal components in an overlapping relationship to form a lap joint within a welding window of the retaining device, a compression mechanism configured to apply a force that is substantially perpendicular to the first and second longitudinal axes of the first and second metal components within the welding window and to move the first and second metal component into alignment along a common axis after application of energy thereto, and an energy source configured to apply laser energy to the first and second metal components within the welding window.

The first metal component is formed from a nickel-titanium alloy and the second metal component is formed from a dissimilar metal alloy. In some embodiments, the second metal component is formed from a cobalt chromium alloy, and in some other embodiments, the second metal component is formed from a stainless steel alloy.

The compression mechanism is adapted to move the first and second metal components together a distance that is about 0.5 to about 2 times the diameter of the first metal component. In embodiments, the retaining device includes a first fixation member for retaining the first metal component and a second fixation member for retaining the second metal component.

The system may include a rotation mechanism that is configured to rotate the first and second metal components between pulses of the laser energy emitted from the energy source.

A method of forming a bimetal medical device in accordance with another aspect of the present disclosure includes: overlapping a first end portion of a first metal component defining a first longitudinal axis with a second end portion of a second metal component defining a second longitudinal axis such that the first and second longitudinal axes are substantially parallel, the first and second portions forming a lap joint; applying a first pulse of laser energy to the lap joint; and compressing the first and second metal components along an axis that is substantially perpendicular to the first and second longitudinal axes of the first and second metal components to align the first and second longitudinal axes of the first and second metal components along a common axis to form a welded region.

In embodiments, a second pulse of laser energy may be applied to the welded region of the first and second metal components. In certain embodiments, the first and second metal component may be rotated before applying the second pulse of laser energy.

DETAILED DESCRIPTION

The following discussion includes a description of systems and methods of forming bimetal medical devices from two dissimilar metal components in accordance with the one or more principles of the present disclosure. For the purposes of discussion, a bimetal medical device will be discussed in terms of a bimetal guidewire; however, the presently disclosed systems and methods may be utilized to form any composite wire or composite structure suitable for use in medical applications.

Figure 1A:
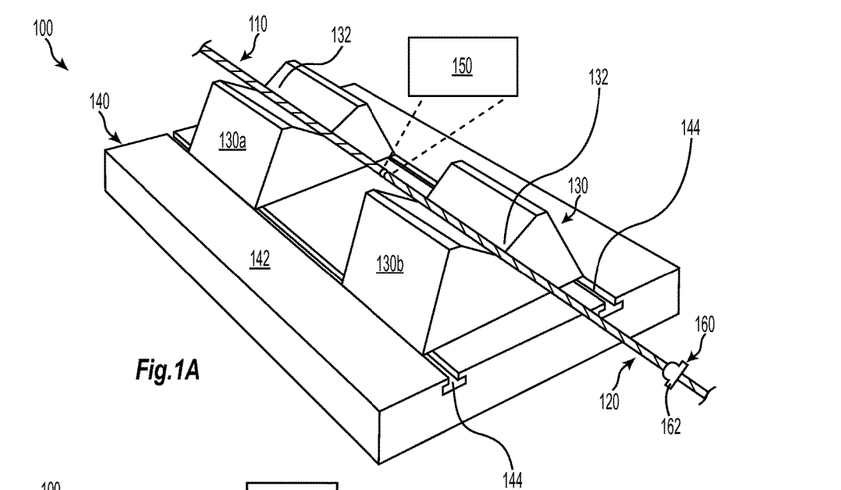
FIGS. 1A and 1B are schematic illustrations showing a perspective view and a side view, respectively, of a system of forming a bimetal guidewire from two dissimilar metal components in accordance with an embodiment of the present disclosure.
Figure 1B:
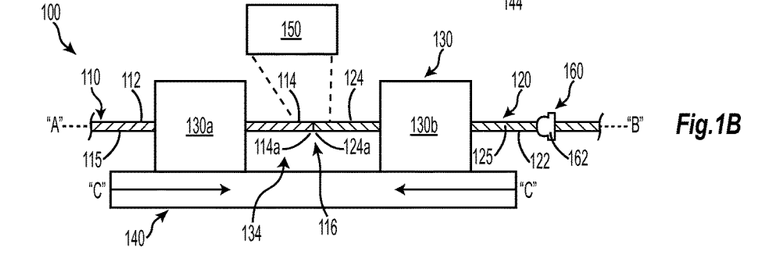

Referring now to the drawings, wherein like reference numerals identify similar or identical elements throughout the several views, FIGS. 1A and 1B illustrate a system 100 of forming a bimetal guidewire. The system 100 includes a first metal component 110, a second metal component 120 and a retaining device 130. The retaining device 130 is configured to releasably retain the first and second metal components 110 and 120 whereby first and second end portions 114 and 124 of the first and second metal components 110 and 120 abut in a pre-determined orientation with respect to each other to form a joint 116. The system 100 further may include a compression mechanism 140 and an energy source 150. The compression mechanism 140 may be adapted to move the first and second end portions 114 and 124 of the first and second metal components 110 and 120 a predetermined distance into each other in a predetermined direction. The energy source 150 may apply laser energy to the abutting first and second end portions 114 and 124 of the first and second metal components 110 and 120 for a predetermined period of time in a predetermined number of pulses. In some embodiments, the system 100 may include a rotation mechanism 160 for rotating the first and second metal components 110 and 120 between pulses.

The first metal component 110 is formed from a metal or metal alloy having a lower modulus of elasticity than the metal or metal alloy of the second metal component 120. In embodiments, the first metal component 110 is formed from a superelastic alloy, such as a nickel titanium alloy. The second metal component 120 is formed from a metal or metal alloy different than the first metal component 110. In embodiments, the second metal component 120 is formed from a cobalt based alloy. In certain embodiments, the second metal component 120 is formed from a cobalt chromium alloy. In embodiments, the second metal component 120 is formed from a stainless steel alloy. It should be understood that the material of the first and second metal components 110 and 120 is not particularly limited and is dictated by the design, usage, and desired properties of the bimetal guidewire 170 (FIG. 1D) formed therefrom.

Figure 1C:
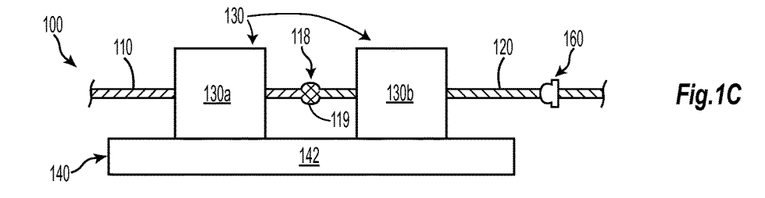
FIG. 1C is a schematic illustration showing a side view of the system of FIGS. 1A and 1B illustrating the two metal components joined at a welded region.
Figure 1D:
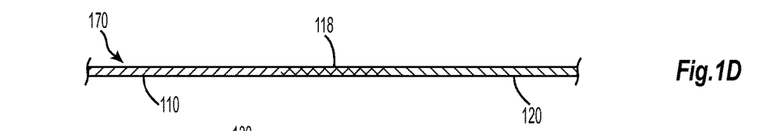
FIG. 1D is a schematic illustration showing a side view of the formed bimetal guidewire of FIG. 1C in accordance with one or more aspects of the present disclosure.

It should also be understood that the first and second metal components 110 and 120 may be any shape and size depending upon the desired performance characteristics of the formed bimetal guidewire 170 (FIG. 1D). The first and second metal components 110 and 120 have substantially the same shape and size so that when they are aligned they are concentric and share the same center or axis. Each of the first and second metal components 110 and 120 includes a cylindrical elongate body 112 and 122 defining a first and second longitudinal axis "A" and "B", respectively. The cylindrical elongate bodies 112 and 122 of the first and second metal components 110 and 120 have substantially the same diameter. The diameter of the first and second metal components 110 and 120 may be from about 0.127 mm to about 0.635 mm. As used herein, the terms "generally", "substantially", and "about" shall be understood as words of approximation that to take into account relatively little to no variation in the modified terms.

The retaining device 130 releasably retains at least a portion of the first and second metal components 110 and 120 in a fixed position. The retaining device 130 may include one or more fixation members 130a and 130b for dependently or independently holding each of the first and second metal components 110 and 120 in a predetermined orientation with respect to each other. In embodiments, each of the fixation members 130a and 130b may include a groove or channel 132 in which the first and second metal component 110 and 120 may be mounted. In other embodiments, the retaining device 130 includes a vise or other gripping and/or jaw member within which the first and second metal components 110 and 120 may be fixed. It should be understood that any structure adapted to releasably retain the first and/or second metal components 110 and 120 in a fixed position may be utilized in accordance with one or more aspects of the present disclosure.

The compression mechanism 140 applies a force on the abutting first and second end portions 114 and 124 of the first and second metal components 110 and 120 held by the retaining device 130. The compression mechanism 140 applies a sufficient amount of pressure on the first and second metal components 110 and 120 to move the first and second metal components 110 and 120 together a distance that is about one-half to about two times the diameter of the first metal component 110 (e.g., the distance may be 0.5, 0.75, 1, 1.25, 1.5, 1.75, and 2 times the diameter of the first metal component 110) after the first and second metal components soften and/or melt from the application of energy thereto. In embodiments, the force is less than 2 kg/mm$^2$.

Figure 2:
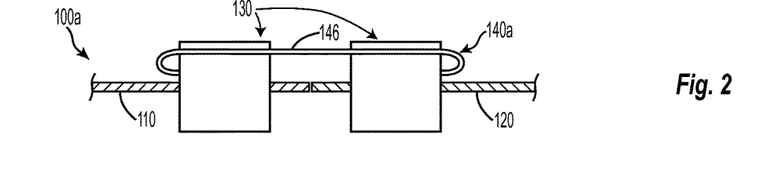
FIG. 2 is a schematic illustration showing a side view of an alternate embodiment of the system of FIG. 1A.

The first and second metal components 110 and 120 may be compressed together by various manual techniques or mechanical and/or motorized devices, such as, for example, band and clamps, among other devices within the purview of those skilled in the art. The compression mechanism 140 may apply a force directly on the first and second metal components 110 and 120, or may apply a force on the retaining device 130, which in turn, applies pressure to the first and second metal components 110 and 120. In embodiments, the compression mechanism 140 may be integrated with the retaining device 110 and may include, for example, a motorized slide 142 for varying the distance between the fixation members 130a and 130b of the retaining device 130. In other embodiments, the compression mechanism 140a may be a separate device, such as a band 146, which may be tightened or loosened around the first and second metal components 110 and 120, and/or the retaining device 130 to apply pressure onto the first and second metal components 110 and 120 over a predetermined distance, as illustrated in the system 110a of FIG. 2.

The energy source 150 applies laser energy to the abutting first and second end portions 114 and 124 of the first and second metal components 110 and 120. The energy source 150 produces visible red light or infrared light. In embodiments, gas lasers provide energy in the mid-to-fair infrared range. Lasers capable of infrared emission include, for example, helium, helium-neon, and carbon dioxide lasers. Other lasers capable of infrared emission include diode lasers, infrared neodymium lasers, and solid state lasers, such as neodymium: YAG lasers. It should be understood that suitable lasers are within the purview of those skilled in the art and include those that are commercially available. It is contemplated that, in alternate embodiments, other types of energy sources may be utilized in a system of the present disclosure.

The laser energy is applied in one or more pulses at a predetermined output over a predetermined period of time. The energy output is defined by the equation:

$$J=5.9DX$$

where, D is the diameter of the first metal component 110 in mm and X is a constant in the range of about 0.5 to about 1.5. The pulse width is from about 5 ms to about 20 ms, and in some embodiments about 10 ms.

In some embodiments, laser energy may be evenly focused on the joint 116 between the first and second metal components 110 and 120. In other embodiments, the laser energy may be focused or directed toward one of the first and second metal components 110 and 120, for example, up to about 75% of the energy may be focused on one of the first and second metal components 110 and 120.

Optionally, a rotation mechanism 160 may be provided to rotate the first and second metal components 110 and 120. The rotation mechanism 160 may include any mechanical and/or motorized devices within the purview of those skilled in the art, including, for example, a spindle 162. The rotation mechanism 160 may be utilized to rotate the first and second metal components 110 and 120 between pulses to expose different portions of the outer surface 115 and 125 of the first and second metal components 110 and 120 to the laser energy emitted from energy source 150.

Referring now to FIGS. 1C and 1D, in conjunction with FIGS. 1A and 1B, the system 100 for laser welding the first and second metal components 110 and 120 to form a bimetal guidewire is illustrated in accordance with an embodiment of the present disclosure. The first metal component 110, which is formed from a nickel titanium alloy, includes a cylindrical elongate body 112 defining a longitudinal axis "A". The first metal component 110 is positioned within a channel 132 of the first fixation member 130a of the retaining device 130 such that a first end portion 114 extends into a welding window 134 defined between the first and second fixation members 130a and 130b of the retaining device 130. The second metal component 120, which is formed from a metal alloy that is not the same as the metal alloy of the first metal component 110, includes a cylindrical elongate body 122 defining a longitudinal axis "B". The second metal component 120 is positioned within a channel 132 of the second fixation member 130b of the retaining device 130 such that a second end portion 124 extends into the welding window 134. The first and second end portions 114 and 124 of the first and second metal components 110 and 120, respectively, are positioned such that first and second end surfaces 114a and 124a are adjacent to each other and are directly touching to form a butt joint 116. The longitudinal axes "A" and "B" of the first and second metal components 110 and 120 are substantially axially aligned along a common axis at least along the first and second end portions 114 and 124 of the first and second metal components 110 and 120 positioned within welding window 134.

The compression mechanism 140 includes a motorized slide block 142 including channels 144 within which a portion of the first and second fixation members 130a and 130b is disposed. The compression mechanism 140 applies an axially inward force in the direction of arrow "C" on the first and second fixation members 130a and 130b to maintain the first and second end portions 114 and 124 of the first and second metal components 110 and 120 in abutting relation and to move the first and second end portions 114 and 124 of the first and second metal components 110 and 120 together a predetermined distance. The predetermined distance may be about one-half to about two times the diameter of the first metal component 110 after the first and second end portions 114 and 124 have been exposed to a laser pulse.

The energy source 150 is positioned a pre-determined distance from the welding window 134 defined between the first and second fixation members 130a and 130b of the retaining device 130. A first pulse having a predetermined laser energy output and pulse width is applied to the butt joint 116, with about 50% to about 75% of the laser energy directed toward the first metal component 110. During the first pulse, the first and second end portions 114 and 124 of the first and second metal components 110 and 120 become pliant with the application of energy. The compression mechanism 140 actuates to move the first and second metal components 110 and 120 together a predetermined distance, as discussed above, to create a welded region 118. (FIG. 1C). The welded region 118 forms a weld bulb 119. Optionally, a second pulse may be applied with about 50% to about 100% of the laser energy focused on the welded region 118. In certain embodiments, the first and second metal components 110 and 120 may be rotated, e.g., about 90°, via the rotation mechanism 160 prior to application of the second pulse.

The welded region 118 may be ground and/or polished by methods within the purview of those skilled in the art, to remove excess or undesired material from the welded region 118. As illustrated in FIG. 1D, welded region 118 of bimetal guidewire 170 is finished so that the welded region 118 has a diameter that is consistent with the native diameter of the first and second metal components 110 and 120.

Figure 3A:
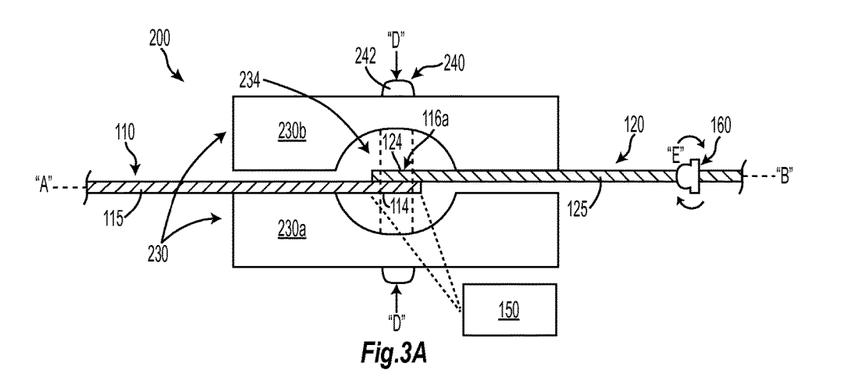
FIG. 3A is a schematic illustration showing a side view of a system of forming a bimetal guidewire from two dissimilar metal components in accordance with an embodiment of the present disclosure.
Figure 3B:
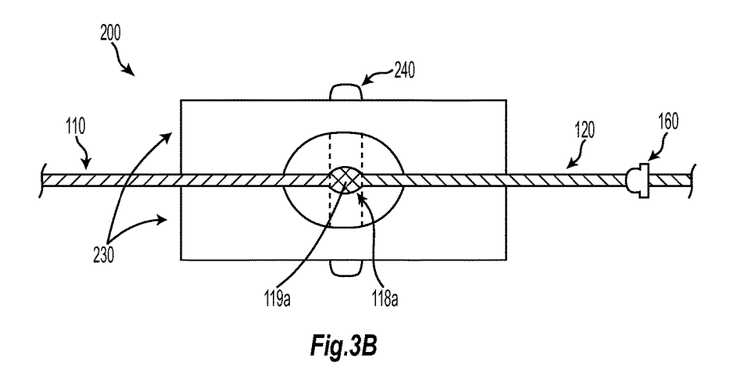
FIG. 3B is a schematic illustration showing a side view of the system of FIG. 3A illustrating the two metal component joined at a welded region.

Referring now to FIGS. 3A and 3B, there is illustrated a system 200 of forming a bimetal guidewire 270 (FIG. 3C) in accordance with another embodiment of the present disclosure. The system 200 is similar to the system 100 of FIG. 1A, and will be described with respect to the differences therebetween. The system 200 includes a first metal component 110, a second metal component 120, a retaining device 230, a compression mechanism 240, an energy source 150, and a rotation mechanism 160.

The first metal component 110 is fixed to a first fixation member 230a of the retaining device 230 and the second metal component 120 is fixed to a second fixation member 230b of the retaining device 230. The first and second end portions 114 and 124 of the first and second metal components 110 and 120 extend into a welding window 234 defined between the first and second fixation members 230a and 230b of the retaining device 230. The first and second end portions 114 and 124 are positioned adjacent to each other such that the longitudinal axes "A" and "B", respectively, of the first and second metal components 110 and 120 are substantially parallel and a portion of an outer surface 115 and 125 of the first and second metal components 110 and 120 are directly touching to form a lap joint 116a.

The compression mechanism 240 includes a clamp 242 for applying a compressive force on the first and second fixation members 230a and 230b of the retaining device 230 in a direction, denoted by arrows "D", that is perpendicular to the longitudinal axes "A" and "B" of the first and second fixation members 230a and 230b of the retaining device 230.

The energy source 150 is positioned a pre-determined distance from the welding window 234 defined between the first and second fixation members 230a and 230b of the retaining device 230. A first pulse having a predetermined laser energy output and pulse width is applied to the lap joint 116a. During the first pulse, the compression mechanism 240 is actuated such that the first and second metal components 110 and 120 move together and the longitudinal axes "A" and "B" of the first and second metal components 110 and 120 become concentric with each other and align along a common axis, as illustrated in FIG. 3B. A welded region 118a having a weld bulb 119a is created between the first and second metal components 110 and 120 by the combination of the compressive force and laser energy exerted on the first and second end portions 114 and 124 of the first and second metal components 110 and 120. Optionally, a second pulse may be applied to the welded region 118a. In certain embodiments, the first and second metal components 110 and 120 are turned, e.g., about 90°, via the rotation mechanism 160 prior to application of the second pulse to aid in the alignment of the first and second metal components 110 and 120 along the common axis.

Figure 3C:
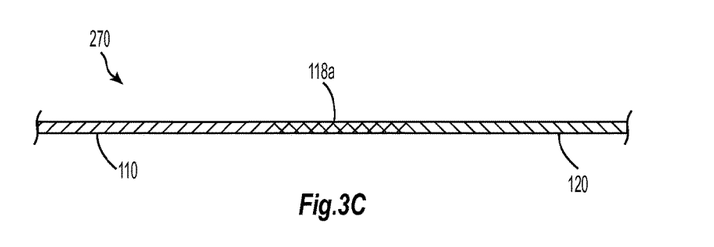
FIG. 3C is a schematic illustration showing a side view of the formed bimetal guidewire of FIG. 3B in accordance with one or more aspects of the present disclosure.

The welded region 118a may be ground and/or polished by methods within the purview of those skilled in the art, to remove excess or undesired material from the welded region 118a. As illustrated in FIG. 3C, the welded region 118a of the bimetal guidewire 270 is finished so that the welded region 118a has a diameter that is consistent with the native diameter of the first and second metal components 110 and 120.

Figure 4A:
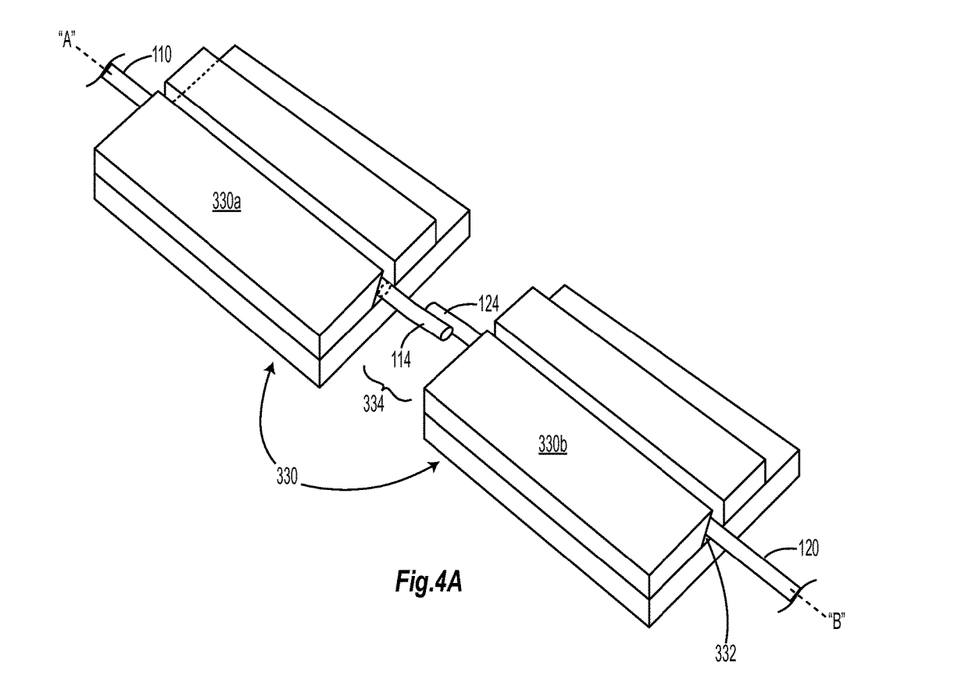
FIGS. 4A and 4B are schematic illustrations showing a perspective view and a cross-sectional view, respectively, of a retaining device and a compression mechanism of the system of FIG. 3A in accordance with an alternate embodiment of the present disclosure.
Figure 4B:
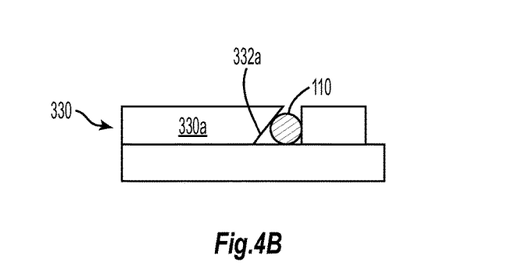

In an alternate embodiment, illustrated in FIGS. 4A and 4B, a retaining device 330 includes first and second fixation members 330a and 330b each including a channel 332 having an angled surface 332a for holding and maintaining each of the first and second metal components 110 in alignment with their respective longitudinal axes "A" and "B". The channels 332 of the first and second fixation members 330a and 33b are aligned such that longitudinal axes "A" and "B" of the first and second metal components 110 and 120 extend along a common axis. As the longitudinal axes "A" and "B" are aligned and the first and second metal components 110 and 120 are biased to extend along the common axis, the first and second end portions 114 and 124 of the first and second metal components 110 and 120 overlap and are deflected away from longitudinal axes "A" and "B" in a welding window 334. Thus, the compression mechanism is provided by a compressive force that is maintained between the deflected first and second end portions 114 and 124. Upon application of energy, the first and second end portions 114 and 124 soften thereby allowing the first and second end portions 114 and 124 to return to their biased, undeflected state along longitudinal axes "A" and "B", melding the first and second end portions 114 and 124 together along the common axis.

Figure 5:
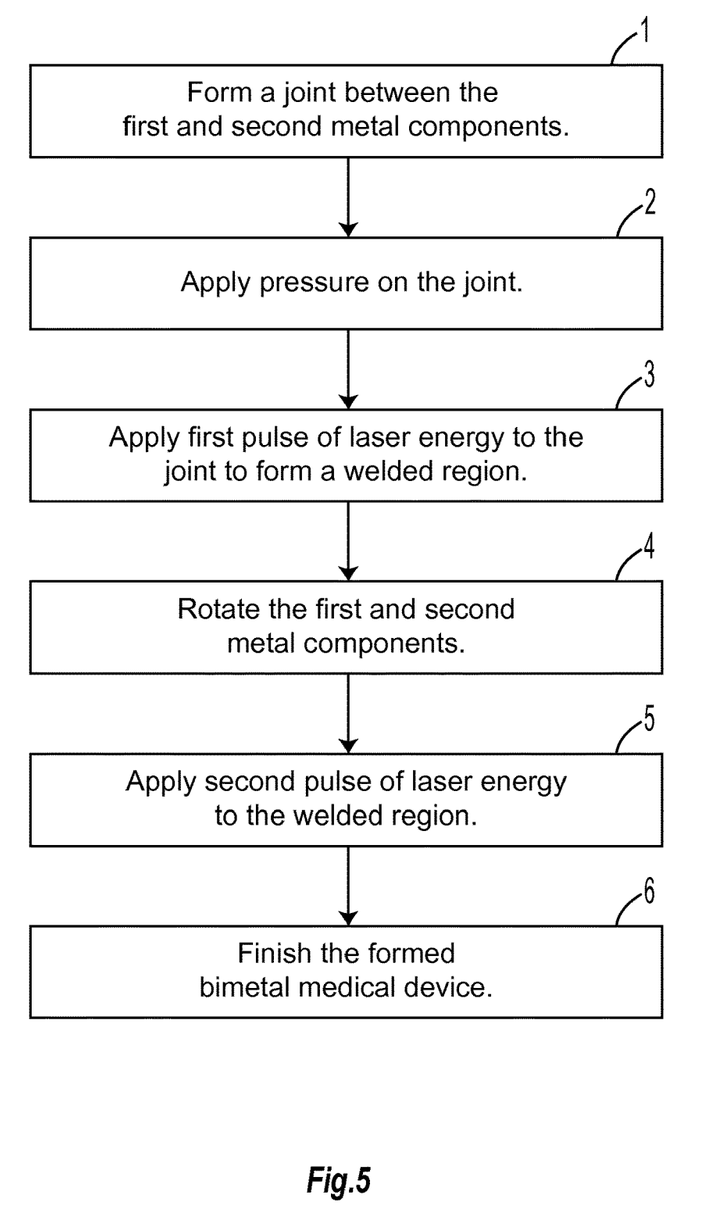
FIG. 5 is a flow chart of a laser welding process in accordance with one or more principles of the present disclosure.

Referring now to the block diagram of FIG. 5, a laser welding process is illustrated for joining the two dissimilar metal components to form a bimetal medical device in accordance with one or more principles of the present disclosure. In step 1, a set-up step, the first and second metal components are placed within a retaining device at a predetermined orientation with respect to each other to form a joint. In some embodiments, the joint is a butt joint, and in some embodiments, the joint is a lap joint. In step 2, uniaxial pressure is applied to the joint formed between the first and second metal components. In embodiments in which the joint is a butt joint, the applied force is directed along the same axis as the aligned longitudinal axes of the first and second metal components. In embodiments in which the joint is a lap joint, the applied force is directed along an axis that is perpendicular to the longitudinal axes of the first and second metal components. A first pulse of laser energy is applied to the joint in step 3 to form a welded region. The combination of the laser energy and compression force forms a weld bulb in the welded region. The now joined first and second metal components may be rotated in step 4 and a second pulse of laser energy may be applied to the welded region in step 5. The formed bimetal medical device may be finished in step 6.

While the above description contains many specifics, these specifics should not be construed as limitations on the scope of the present disclosure, but merely as exemplifications of embodiments thereof. It is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Those skilled in the art will envision many other possible variations that are within the scope and spirit of the present disclosure.

What is claimed is:

1. A system of forming a bimetal medical device, which comprises:
   a first metal component defining a first longitudinal axis and including a first end portion, wherein the first metal component comprises a nickel-titanium alloy;
   a second metal component defining a second longitudinal axis and including a second end portion, wherein the second metal component comprises a cobalt chromium alloy or a stainless steel alloy;
   a retaining device configured to retain the first and second end portions of the first and second metal components in an abutting relationship to form a butt joint within a welding window, wherein the retaining device comprises a first fixation member for retaining the first metal component and a second fixation member for retaining the second metal component, wherein the welding window is defined between the first fixation member and the second fixation member of the retaining device;
   a compression mechanism configured to apply an axially inward force to move the first and second metal components axially together; and
   an energy source configured to apply energy directed to both the first and second end portions of the first and second metal components within the welding window, the energy applied being determined by the equation:

$$\text{Joules} = 5.9DX$$

wherein D=diameter (mm) of the first metal component and X=0.5-1.5.

2. The system according to claim 1, wherein the compression mechanism is adapted to move the first and second metal components a distance that is about 0.5 to about 2 times a diameter of the first metal component.

3. The system according to claim 1, further comprising a rotation mechanism configured to rotate the first and second metal components between pulses of energy emitted from the energy source.

4. The system according to claim 1, wherein the energy source emits laser energy.

5. A method of forming a bimetal medical device comprising:
   retaining a first metal component using a first fixation member of a retaining device, wherein the first metal component comprises a nickel-titanium alloy;
   retaining a second metal component using a second fixation member of the retaining device, wherein the second metal component comprises a cobalt chromium alloy or a stainless steel alloy;
   applying a first pulse of laser energy directed to both abutting first and second end portions of the first and second metal components aligned along a common axis, the first and second end portions forming a butt joint within a welding window defined between the first fixation member and the second fixation member of the retaining device, the laser energy applied determined by the equation:

$$\text{Joules} = 5.9DX$$

wherein D=diameter (mm) of the first metal component and X=0.5-1.5; and
   compressing the first and second metal components axially together to form a welded region between the first and second metal components.

6. The method of claim 5, wherein compressing the first and second metal components further includes moving the first and second metal components together a distance that is about 0.5 to about 2 times a diameter of the first metal component.

7. The method of claim 5, further comprising applying a second pulse of laser energy to the welded region of the first and second metal components.

8. The method of claim 7, further comprising rotating the first and second metal components before applying the second pulse of laser energy.

9. The system of claim 1, wherein the compression mechanism is adapted to apply the axially inward force directly on both the first and second metal components.

10. The system of claim 1, wherein the energy source is directed to apply energy evenly to both the first and second end portions in the joint within the welding window.

11. The system of claim 1, wherein the energy source is directed to apply between about 50% and about 7% of the energy to one of the first and second end portions and the remainder of the energy to the other of the first and second end portions.

* * * * *